(12) United States Patent
Cyncynatus et al.

(10) Patent No.: US 8,101,190 B2
(45) Date of Patent: Jan. 24, 2012

(54) METHOD FOR DIAGNOSING STAPHYLOCOCCAL INFECTIONS

(75) Inventors: Camille Cyncynatus, Antony (FR); Julie Roge, Paris (FR); Damien Thomas, Lucenay (FR); Helene Nuyttens, Antony (FR)

(73) Assignee: Ingen Biosciences, Chilly Mazarin (FR)

( * ) Notice: Subject to any disclaimer, the term of this patent is extended or adjusted under 35 U.S.C. 154(b) by 0 days.

(21) Appl. No.: 12/396,924

(22) Filed: Mar. 3, 2009

(65) Prior Publication Data

US 2010/0227810 A1   Sep. 9, 2010

(51) Int. Cl.
- A61K 39/09 (2006.01)
- A61K 39/02 (2006.01)
- A61K 39/00 (2006.01)
- C12Q 1/00 (2006.01)
- G01N 33/553 (2006.01)
- G01N 33/554 (2006.01)

(52) U.S. Cl. .............. 424/237.1; 424/184.1; 424/185.1; 424/234.1; 435/4; 435/7.1; 435/7.32; 435/7.33

(58) Field of Classification Search .................. None
See application file for complete search history.

(56) References Cited

U.S. PATENT DOCUMENTS

| | | | |
|---|---|---|---|
| 5,700,928 A | 12/1997 | Hodgson et al. | |
| 6,380,370 B1 | 4/2002 | Doucette-Stamm et al. | |
| 6,703,492 B1 | 3/2004 | Kimmerly | |
| 6,936,258 B1 * | 8/2005 | Pavliak et al. | 424/243.1 |
| 7,410,647 B2 | 8/2008 | Foster et al. | |
| 7,608,276 B2 | 10/2009 | Masignani et al. | |
| 2003/0186275 A1 | 10/2003 | Foster et al. | |
| 2004/0147734 A1* | 7/2004 | Doucette-Stamm et al. | 536/23.7 |
| 2005/0255478 A1 | 11/2005 | Kimmerly | |
| 2009/0269349 A1 | 10/2009 | Foster et al. | |
| 2010/0047267 A1 | 2/2010 | Masignani et al. | |
| 2010/0055130 A1 | 3/2010 | Masignani et al. | |

FOREIGN PATENT DOCUMENTS

| | | |
|---|---|---|
| FR | 2908890 | 5/2008 |
| WO | 2006/005825 | 1/2006 |

OTHER PUBLICATIONS

Greenspan et al, Nature Biotechnology 17:936-937, 1999.*
Houghten et al. (New Approaches to Immunization, Vaccines 86, Cold Spring Harbor Laboratory, p. 21-25, 1986).*
Colman et al. (Research in Immunology 145: 33-36, 1994.*
Mendoza et al. International Journal of Systemic Bacteriology, 1988, 48:1049-1055, p. 1051.*
Defintion of Kit: http://oxforddictionaries.com/search?q=kit &view=uk.*
Bornstein, N. et al., "Immune response to staphylococcal toxins and ribitol teichoic acid in *Staphylococcus aureus* infections," Med. Microbiol. Lett. (1992) 1:111-119.
Christensson, B. et al., "Diagnosing *Staphylococcus aureus* endocarditis by detecting antibodies against *S. aureus* capsular polysaccharide types 5 and 8," J. Infect. Dis. 163:530-533 (1993).
Database Accession Gene ID No. 1055884, SE0750 N-acetylmuramoyl-L-alanine amidase [*Staphylococcus epidermidis* ATCC 12228], http://www.ncbi.nlm.nih.gov/gene?term=1055684 (updated Apr. 17, 2010) 2 pages.
Database Accession No. 1056712, "SE0405 lipoprotein [*Staphylococcus epidermidis* ATCC 12228]," http://www.ncbi.nlm.nih.gov/gene?term=1056712 (Jul. 26, 2010) 2 pages.
Database Accession No. AAO04002.1, GI:27314866, "Lipoprotein [*Staphylococcus epidermidis* ATCC 12228]," http://www.ncbi.nlm.nih.gov/protein/27314866 (Mar. 5, 2010) 1 page.
Database Accession No. AAO04347.1, GI:27315212, "N-acetylmuramoyl-L-alanine amidase [*Staphylococcus epidermidis* ATCC 12228]," http://www.ncbi.nlm.nih.gov/protein/27315212 (Mar. 5, 2010) 2 pages.
Database Accession No. NP_763960.1, GI:27467323, "lipoprotein [*Staphylococcus epidermidis* ATCC 12228]," http://www.ncbi.nlm.nih.gov/protein/27467323 (Mar. 30, 2010) 1 page.
Database Accession No. NP_764305.1, GI:27467668, "N-acetylmuramoyl-L-alanine amidase [*Staphylococcus epidermidis* ATCC 12228]," http://www.ncbi.nlm.nih.gov/protein/27467668 (Mar. 30, 2010) 2 pages.
Database Accession No. Q7CCL6, http://www.uniprot.org/uniprot/Q7CCL6.txt (Jul. 5, 2004) 1 page.
Database Accession No. Q8CPQ1, http://www.uniprot.org/uniprot/Q8CPQ1.txt (Mar. 1, 2003) 3 pages.
Database EMBL Accession No. SEU71377, "*Staphylococcus epidermidis* autolysin AtlE and putative transcriptional regulator AtlR genes, complete cds," http://www.ncbi.nlm.nih.gov/nuccore/2267238 (Jul. 21, 1997) 4 pages.

* cited by examiner

*Primary Examiner* — Oluwatosin Ogunbiyi
(74) *Attorney, Agent, or Firm* — Michael Best & Friedrich LLP

(57) ABSTRACT

The present invention relates to a method for determining if an individual is infected by a *staphylococcus bacterium*, comprising:
- determining if antibodies directed against at least 2 proteins comprising a sequence selected from the group consisting of SEQ ID NO: 2, SEQ ID NO: 4, and SEQ ID NO: 6, are present in a biological sample of the individual, and
- deducing therefrom that the individual is infected by a *staphylococcus bacterium*.

15 Claims, No Drawings

SEQUENCE LISTING

```
<160> NUMBER OF SEQ ID NOS: 12

<210> SEQ ID NO 1
<211> LENGTH: 561
<212> TYPE: DNA
<213> ORGANISM: Staphylococcus epidermidis

<400> SEQUENCE: 1
ggaactaata ataagttaac tgtgtctgct aatcgtggtg ttgctcaaat taaaccaaca      60
aataatggct tatatacaac tgtttatgac agtaaaggtc ataagactga tcaagtacaa     120
aaaaccctat ccgttactaa aactgcaaca ttaggaaata acaaattcta tttagttgaa     180
gactacaata gcggtaaaaa atacggttgg gttaaacaag gtggtgttgt ttataacact     240
gctaaggcac cagtaaaagt gaatcaaaca tataatgtta aagcagggtc aacactttac     300
acagttcctt ggggtacacc aaaacaagtt gctagcaaag tatctggtac tggaaatcaa     360
acatttaaag caactaaaca gcaacaaatt gataaagcaa cgtatcttta tggtacagtg     420
aatggtaaat ctggttggat tagtaaatat tacttaacta cagcatctaa acctagcaat     480
ccaactaaac cttcaacaaa caaccaatta acagtgacta acaatagtgg tgttgctcaa     540
atcaatgcaa aaaatagtgg c                                              561

<210> SEQ ID NO 2
<211> LENGTH: 187
<212> TYPE: PRT
<213> ORGANISM: Staphylococcus epidermidis

<400> SEQUENCE: 2

Gly Thr Asn Asn Lys Leu Thr Val Ser Ala Asn Arg Gly Val Ala Gln
1               5                   10                  15

Ile Lys Pro Thr Asn Asn Gly Leu Tyr Thr Thr Val Tyr Asp Ser Lys
            20                  25                  30

Gly His Lys Thr Asp Gln Val Gln Lys Thr Leu Ser Val Thr Lys Thr
```

```
                35                  40                  45
Ala Thr Leu Gly Asn Asn Lys Phe Tyr Leu Val Glu Asp Tyr Asn Ser
 50                  55                  60

Gly Lys Lys Tyr Gly Trp Val Lys Gln Gly Gly Val Val Tyr Asn Thr
 65                  70                  75                  80

Ala Lys Ala Pro Val Lys Val Asn Gln Thr Tyr Asn Val Lys Ala Gly
                 85                  90                  95

Ser Thr Leu Tyr Thr Val Pro Trp Gly Thr Pro Lys Gln Val Ala Ser
            100                 105                 110

Lys Val Ser Gly Thr Gly Asn Gln Thr Phe Lys Ala Thr Lys Gln Gln
            115                 120                 125

Gln Ile Asp Lys Ala Thr Tyr Leu Tyr Gly Thr Val Asn Gly Lys Ser
        130                 135                 140

Gly Trp Ile Ser Lys Tyr Tyr Leu Thr Thr Ala Ser Lys Pro Ser Asn
145                 150                 155                 160

Pro Thr Lys Pro Ser Thr Asn Asn Gln Leu Thr Val Thr Asn Asn Ser
                165                 170                 175

Gly Val Ala Gln Ile Asn Ala Lys Asn Ser Gly
            180                 185
```

<210> SEQ ID NO 3
<211> LENGTH: 876
<212> TYPE: DNA
<213> ORGANISM: Staphylococcus epidermidis

<400> SEQUENCE: 3

```
tgtgggaatc acagtaacca tgaacatcac tcacatgaag gaaaattaaa agttgtaact    60
acaaactcta ttctctatga catggttaaa cgtgtcggtg aaataaggt cgatgttcat    120
agcatcgttc cagtaggaca agacccacat gaatatgagg ttaaacctaa agatattaaa   180
gcattaacag atgctgacgt tgtattttat aacggtttaa acctagaaac tggaaatggt   240
tggtttgaaa aagcacttga ccaagcagga aaatcaacaa agataaaaa tgtgatagca   300
gcatcaaata atgttaaacc aatatactta aatggtgagg aaggtaacaa aaacaaacaa   360
gatccacatg catggttaag tttagagaat ggaattaaat acgtaaaaac agtacaaaaa   420
tcactagaac atcatgataa aaagataag tctacatatg aaaaacaagg gaatgcatat   480
atatcaaaat tagaagaact taataaagat agtaaaaata aatttgatga catacccaaa   540
aatcaacgtg ccatgatgac aagtgaaggt gcatttaaat attttgctca acaattcgat   600
gttaaaccag ttatatttg ggagataaac acagaaaaac aaggtacacc tggtcaaatg   660
aaacaagcca ttaaatttgt taagataat catttaaaac attattagt cgaaacaagc   720
gtagataaaa aagctatgca agtttatca gaagaaacta gaaagatat ttatggtgaa   780
gtatttaccg actctatagg taaggaaggt actaaaggtg actcatacta taaaatgatg   840
aaatctaata ttgatacaat acatggtagt atgaaa                             876
```

<210> SEQ ID NO 4
<211> LENGTH: 292
<212> TYPE: PRT
<213> ORGANISM: Staphylococcus epidermidis

<400> SEQUENCE: 4

```
Cys Gly Asn His Ser Asn His Glu His His Ser His Glu Gly Lys Leu
 1               5                  10                  15

Lys Val Val Thr Thr Asn Ser Ile Leu Tyr Asp Met Val Lys Arg Val
             20                  25                  30
```

```
Gly Gly Asn Lys Val Asp Val His Ser Ile Val Pro Val Gly Gln Asp
        35                  40                  45

Pro His Glu Tyr Glu Val Lys Pro Lys Asp Ile Lys Ala Leu Thr Asp
    50                  55                  60

Ala Asp Val Val Phe Tyr Asn Gly Leu Asn Leu Glu Thr Gly Asn Gly
65                  70                  75                  80

Trp Phe Glu Lys Ala Leu Asp Gln Ala Gly Lys Ser Thr Lys Asp Lys
                85                  90                  95

Asn Val Ile Ala Ala Ser Asn Asn Val Lys Pro Ile Tyr Leu Asn Gly
            100                 105                 110

Glu Gly Asn Lys Asn Lys Gln Asp Pro His Ala Trp Leu Ser Leu
        115                 120                 125

Glu Asn Gly Ile Lys Tyr Val Lys Thr Ile Gln Lys Ser Leu Glu His
    130                 135                 140

His Asp Lys Lys Asp Lys Ser Thr Tyr Glu Lys Gln Gly Asn Ala Tyr
145                 150                 155                 160

Ile Ser Lys Leu Glu Glu Leu Asn Lys Asp Ser Lys Asn Lys Phe Asp
                165                 170                 175

Asp Ile Pro Lys Asn Gln Arg Ala Met Met Thr Ser Glu Gly Ala Phe
            180                 185                 190

Lys Tyr Phe Ala Gln Gln Phe Asp Val Lys Pro Gly Tyr Ile Trp Glu
        195                 200                 205

Ile Asn Thr Glu Lys Gln Gly Thr Pro Gly Gln Met Lys Gln Ala Ile
    210                 215                 220

Lys Phe Val Lys Asp Asn His Leu Lys His Leu Leu Val Glu Thr Ser
225                 230                 235                 240

Val Asp Lys Lys Ala Met Gln Ser Leu Ser Glu Thr Lys Lys Asp
                245                 250                 255

Ile Tyr Gly Glu Val Phe Thr Asp Ser Ile Gly Lys Gly Thr Lys
        260                 265                 270

Gly Asp Ser Tyr Tyr Lys Met Met Lys Ser Asn Ile Asp Thr Ile His
    275                 280                 285

Gly Ser Met Lys
    290

<210> SEQ ID NO 5
<211> LENGTH: 834
<212> TYPE: DNA
<213> ORGANISM: Staphylococcus aureus

<400> SEQUENCE: 5
ttaaaagtag taacgacgaa ttcaatttta tatgatatgg ctaaaatgt tggtggagac     60 aacgtcgata ttcatagtat tgtacctgtt ggtcaagatc ctcatgaata tgaagttaaa    120
cctaaagata ttaaaagtt aactgacgct gacgttattt tatacaacgg attaaattta    180
gagactggta acggttggtt tgaaaaagcc ttagaacagg ctggtaaatc attaaaagat    240
aaaaaagtta tcgcagtatc aaaagatgtt aaacctatct atttaaacgg tgaagaaggc    300
aacaaagata acaagatcc acacgcatgg ttaagtttag ataatggtat taaatacgta    360
aaaacaattc aacaaacatt tatcgataac gacaaaaaac ataaagcaga ttatgaaaag    420
caaggtaaca aatacattgc tcaattggaa aaattaaata tgacagtaa agacaaattt    480 aatgacattc caaagaaca acgtgccatg attacaagtg aaggtgcctt caagtacttc    540
tcaaaacaat acggtattac accaggttat atttgggaaa ttaacactga aaaacaaggt    600
```

| acacctgaac aaatgagaca agctattgag tttgttaaaa agcacaaatt aaaacactta | 660 |
| ttagtagaaa caagtgttga taagaaagca atggaaagtt tatctgaaga aacgaagaaa | 720 |
| gatatctttg gtgaagtgta cacagattca atcggtaaag aaggcactaa aggtgactct | 780 |
| tactacaaaa tgatgaaatc aaatattgaa actgtacacg gaagcatgaa ataa | 834 |

<210> SEQ ID NO 6
<211> LENGTH: 277
<212> TYPE: PRT
<213> ORGANISM: Staphylococcus aureus

<400> SEQUENCE: 6

```
Leu Lys Val Val Thr Thr Asn Ser Ile Leu Tyr Asp Met Ala Lys Asn
1               5                   10                  15

Val Gly Gly Asp Asn Val Asp Ile His Ser Ile Val Pro Val Gly Gln
            20                  25                  30

Asp Pro His Glu Tyr Glu Val Lys Pro Lys Asp Ile Lys Lys Leu Thr
        35                  40                  45

Asp Ala Asp Val Ile Leu Tyr Asn Gly Leu Asn Leu Glu Thr Gly Asn
    50                  55                  60

Gly Trp Phe Glu Lys Ala Leu Glu Gln Ala Gly Lys Ser Leu Lys Asp
65                  70                  75                  80

Lys Lys Val Ile Ala Val Ser Lys Asp Val Lys Pro Ile Tyr Leu Asn
                85                  90                  95

Gly Glu Glu Gly Asn Lys Asp Lys Gln Asp Pro His Ala Trp Leu Ser
            100                 105                 110

Leu Asp Asn Gly Ile Lys Tyr Val Lys Thr Ile Gln Gln Thr Phe Ile
        115                 120                 125

Asp Asn Asp Lys Lys His Lys Ala Asp Tyr Glu Lys Gln Gly Asn Lys
    130                 135                 140

Tyr Ile Ala Gln Leu Glu Lys Leu Asn Asn Asp Ser Lys Asp Lys Phe
145                 150                 155                 160

Asn Asp Ile Pro Lys Glu Gln Arg Ala Met Ile Thr Ser Glu Gly Ala
                165                 170                 175

Phe Lys Tyr Phe Ser Lys Gln Tyr Gly Ile Thr Pro Gly Tyr Ile Trp
            180                 185                 190

Glu Ile Asn Thr Glu Lys Gln Gly Thr Pro Glu Gln Met Arg Gln Ala
        195                 200                 205

Ile Glu Phe Val Lys Lys His Lys Leu Lys His Leu Leu Val Glu Thr
    210                 215                 220

Ser Val Asp Lys Lys Ala Met Glu Ser Leu Ser Glu Glu Thr Lys Lys
225                 230                 235                 240

Asp Ile Phe Gly Glu Val Tyr Thr Asp Ser Ile Gly Lys Glu Gly Thr
                245                 250                 255

Lys Gly Asp Ser Tyr Tyr Lys Met Met Lys Ser Asn Ile Glu Thr Val
            260                 265                 270

His Gly Ser Met Lys
        275
```

<210> SEQ ID NO 7
<211> LENGTH: 939
<212> TYPE: DNA
<213> ORGANISM: Staphylococcus aureus

<400> SEQUENCE: 7

| ttatcatcaa aagctatgga caatcatcca caacaaacgc agtcaagcaa acagcaaaca | 60 |

```
cctaagatta aaaaaggcgg taaccttaaa ccattagaac aacgtgaaca cgcaaatgtt    120
atattaccga ataacgatcg tcaccaaatc acagatacaa cgaatggtca ttatgcaccc    180
gtaacttata ttcaagttga agcacctact ggtacattta ttgcttccgg tgtagttgta    240
ggtaaagata ctcttttaac aaataaacac gtcgtagatg ctacgcacgg tgatcctcat    300
gctttaaaag cattcccttc tgcaattaac caagacaatt atccaaatgg tggtttcact    360
gctgaacaaa tcactaaata ttcaggcgaa ggtgatttag caatagttaa attctcccct    420
aatgagcaaa acaaacatat tggtgaagta gttaaaccag caacaatgag taataatgct    480
gaaacacaag ttaaccaaaa tattactgta acaggatatc ctggtgataa acctgtagca    540
acaatgtggg aaagtaaagg aaaaatcact tacctcaaag gcgaagctat gcaatatgat    600
ttaagtacaa ctggtggtaa ctcaggttca cctgtattta tgaaaaaaa tgaagtgatc    660 ggaattcatt ggggcggtgt accaaatgaa tttaatggtg cggtatttat taatgaaaat    720
gtacgcaact tcttaaaaca aaatattgaa gatatccatt ttgccaacga tgaccaacct    780
aataacccag ataatcctga taaccctaac aatcctgata accctaacaa tcctgataac    840
cctaacaacc cagatgaacc aaataaccct gacaacccta caaccctga taatccagac    900 aatggcgata acaataattc agacaaccct gacgctgca                          939

<210> SEQ ID NO 8
<211> LENGTH: 313
<212> TYPE: PRT
<213> ORGANISM: Staphylococcus aureus

<400> SEQUENCE: 8

Leu Ser Ser Lys Ala Met Asp Asn His Pro Gln Gln Thr Gln Ser Ser
1               5                   10                  15

Lys Gln Gln Thr Pro Lys Ile Lys Lys Gly Gly Asn Leu Lys Pro Leu
                20                  25                  30

Glu Gln Arg Glu His Ala Asn Val Ile Leu Pro Asn Asn Asp Arg His
            35                  40                  45

Gln Ile Thr Asp Thr Thr Asn Gly His Tyr Ala Pro Val Thr Tyr Ile
        50                  55                  60

Gln Val Glu Ala Pro Thr Gly Thr Phe Ile Ala Ser Gly Val Val Val
65                  70                  75                  80

Gly Lys Asp Thr Leu Leu Thr Asn Lys His Val Val Asp Ala Thr His
                85                  90                  95

Gly Asp Pro His Ala Leu Lys Ala Phe Pro Ser Ala Ile Asn Gln Asp
            100                 105                 110

Asn Tyr Pro Asn Gly Gly Phe Thr Ala Glu Gln Ile Thr Lys Tyr Ser
        115                 120                 125

Gly Glu Gly Asp Leu Ala Ile Val Lys Phe Ser Pro Asn Glu Gln Asn
    130                 135                 140

Lys His Ile Gly Glu Val Val Lys Pro Ala Thr Met Ser Asn Asn Ala
145                 150                 155                 160

Glu Thr Gln Val Asn Gln Asn Ile Thr Val Thr Gly Tyr Pro Gly Asp
                165                 170                 175

Lys Pro Val Ala Thr Met Trp Glu Ser Lys Gly Lys Ile Thr Tyr Leu
            180                 185                 190

Lys Gly Glu Ala Met Gln Tyr Asp Leu Ser Thr Thr Gly Gly Asn Ser
        195                 200                 205

Gly Ser Pro Val Phe Asn Glu Lys Asn Glu Val Ile Gly Ile His Trp
    210                 215                 220
```

```
Gly Gly Val Pro Asn Glu Phe Asn Gly Ala Val Phe Ile Asn Glu Asn
225                 230                 235                 240

Val Arg Asn Phe Leu Lys Gln Asn Ile Glu Asp Ile His Phe Ala Asn
                245                 250                 255

Asp Asp Gln Pro Asn Asn Pro Asp Asn Pro Asp Asn Pro Asn Asn Pro
            260                 265                 270

Asp Asn Pro Asn Asn Pro Asp Asn Pro Asn Asn Pro Asp Glu Pro Asn
        275                 280                 285

Asn Pro Asp Asn Pro Asn Asn Pro Asp Asn Pro Asp Asn Gly Asp Asn
    290                 295                 300

Asn Asn Ser Asp Asn Pro Asp Ala Ala
305                 310
```

<210> SEQ ID NO 9
<211> LENGTH: 209
<212> TYPE: PRT
<213> ORGANISM: Artificial sequence
<220> FEATURE:
<223> OTHER INFORMATION: S. epidermidis antigen + purification tag

<400> SEQUENCE: 9

```
Met Ser Tyr Tyr His His His His His His Leu Glu Ser Thr Ser Leu
1               5                   10                  15

Tyr Lys Lys Ala Gly Leu Gly Thr Asn Asn Lys Leu Thr Val Ser Ala
                20                  25                  30

Asn Arg Gly Val Ala Gln Ile Lys Pro Thr Asn Asn Gly Leu Tyr Thr
            35                  40                  45

Thr Val Tyr Asp Ser Lys Gly His Lys Thr Asp Gln Val Gln Lys Thr
        50                  55                  60

Leu Ser Val Thr Lys Thr Ala Thr Leu Gly Asn Asn Lys Phe Tyr Leu
65                  70                  75                  80

Val Glu Asp Tyr Asn Ser Gly Lys Lys Tyr Gly Trp Val Lys Gln Gly
                85                  90                  95

Gly Val Val Tyr Asn Thr Ala Lys Ala Pro Val Lys Val Asn Gln Thr
            100                 105                 110

Tyr Asn Val Lys Ala Gly Ser Thr Leu Tyr Thr Val Pro Trp Gly Thr
        115                 120                 125

Pro Lys Gln Val Ala Ser Lys Val Ser Gly Thr Gly Asn Gln Thr Phe
    130                 135                 140

Lys Ala Thr Lys Gln Gln Gln Ile Asp Lys Ala Thr Tyr Leu Tyr Gly
145                 150                 155                 160

Thr Val Asn Gly Lys Ser Gly Trp Ile Ser Lys Tyr Tyr Leu Thr Thr
                165                 170                 175

Ala Ser Lys Pro Ser Asn Pro Thr Lys Pro Ser Thr Asn Asn Gln Leu
            180                 185                 190

Thr Val Thr Asn Asn Ser Gly Val Ala Gln Ile Asn Ala Lys Asn Ser
        195                 200                 205

Gly
```

<210> SEQ ID NO 10
<211> LENGTH: 314
<212> TYPE: PRT
<213> ORGANISM: Artificial sequence
<220> FEATURE:
<223> OTHER INFORMATION: S. epidermidis antigen + purification tag

<400> SEQUENCE: 10

Met Ser Tyr Tyr His His His His His His Leu Glu Ser Thr Ser Leu

```
             1               5                  10                 15
Tyr Lys Lys Ala Gly Ser Cys Gly Asn His Ser Asn His Glu His His
                    20                  25                  30

Ser His Glu Gly Lys Leu Lys Val Val Thr Thr Asn Ser Ile Leu Tyr
            35                  40                  45

Asp Met Val Lys Arg Val Gly Gly Asn Lys Val Asp Val His Ser Ile
        50                  55                  60

Val Pro Val Gly Gln Asp Pro His Glu Tyr Glu Val Lys Pro Lys Asp
65                  70                  75                  80

Ile Lys Ala Leu Thr Asp Ala Asp Val Val Phe Tyr Asn Gly Leu Asn
                85                  90                  95

Leu Glu Thr Gly Asn Gly Trp Phe Glu Lys Ala Leu Asp Gln Ala Gly
            100                 105                 110

Lys Ser Thr Lys Asp Lys Asn Val Ile Ala Ala Ser Asn Asn Val Lys
        115                 120                 125

Pro Ile Tyr Leu Asn Gly Glu Glu Gly Asn Lys Asn Lys Gln Asp Pro
    130                 135                 140

His Ala Trp Leu Ser Leu Glu Asn Gly Ile Lys Tyr Val Lys Thr Val
145                 150                 155                 160

Gln Lys Ser Leu Glu His His Asp Lys Lys Asp Lys Ser Thr Tyr Glu
                165                 170                 175

Lys Gln Gly Asn Ala Tyr Ile Ser Lys Leu Glu Glu Leu Asn Lys Asp
            180                 185                 190

Ser Lys Asn Lys Phe Asp Asp Ile Pro Lys Asn Gln Arg Ala Met Met
        195                 200                 205

Thr Ser Glu Gly Ala Phe Lys Tyr Phe Ala Gln Gln Phe Asp Val Lys
    210                 215                 220

Pro Gly Tyr Ile Trp Glu Ile Asn Thr Glu Lys Gln Gly Thr Pro Gly
225                 230                 235                 240

Gln Met Lys Gln Ala Ile Lys Phe Val Lys Asp Asn His Leu Lys His
                245                 250                 255

Leu Leu Val Glu Thr Ser Val Asp Lys Lys Ala Met Gln Ser Leu Ser
            260                 265                 270

Glu Glu Thr Lys Lys Asp Ile Tyr Gly Glu Val Phe Thr Asp Ser Ile
        275                 280                 285

Gly Lys Glu Gly Thr Lys Gly Asp Ser Tyr Tyr Lys Met Met Lys Ser
    290                 295                 300

Asn Ile Asp Thr Ile His Gly Ser Met Lys
305                 310

<210> SEQ ID NO 11
<211> LENGTH: 298
<212> TYPE: PRT
<213> ORGANISM: Artificial sequence
<220> FEATURE:
<223> OTHER INFORMATION: S. aureus antigen + purification tag

<400> SEQUENCE: 11

Met Ser Tyr Tyr His His His His His His Leu Glu Ser Thr Ser Leu
1               5                   10                  15

Tyr Lys Lys Ala Gly Leu Lys Val Val Thr Thr Asn Ser Ile Leu Tyr
                20                  25                  30

Asp Met Ala Lys Asn Val Gly Gly Asp Asn Val Asp Ile His Ser Ile
            35                  40                  45

Val Pro Val Gly Gln Asp Pro His Glu Tyr Glu Val Lys Pro Lys Asp
        50                  55                  60
```

```
Ile Lys Lys Leu Thr Asp Ala Asp Val Ile Leu Tyr Asn Gly Leu Asn
 65                  70                  75                  80

Leu Glu Thr Gly Asn Gly Trp Phe Glu Lys Ala Leu Glu Gln Ala Gly
                 85                  90                  95

Lys Ser Leu Lys Asp Lys Lys Val Ile Ala Val Ser Lys Asp Val Lys
            100                 105                 110

Pro Ile Tyr Leu Asn Gly Glu Glu Gly Asn Lys Asp Lys Gln Asp Pro
        115                 120                 125

His Ala Trp Leu Ser Leu Asp Asn Gly Ile Lys Tyr Val Lys Thr Ile
    130                 135                 140

Gln Gln Thr Phe Ile Asp Asn Asp Lys Lys His Lys Ala Asp Tyr Glu
145                 150                 155                 160

Lys Gln Gly Asn Lys Tyr Ile Ala Gln Leu Glu Lys Leu Asn Asn Asp
                165                 170                 175

Ser Lys Asp Lys Phe Asn Asp Ile Pro Lys Glu Gln Arg Ala Met Ile
            180                 185                 190

Thr Ser Glu Gly Ala Phe Lys Tyr Phe Ser Lys Gln Tyr Gly Ile Thr
        195                 200                 205

Pro Gly Tyr Ile Trp Glu Ile Asn Thr Glu Lys Gln Gly Thr Pro Glu
    210                 215                 220

Gln Met Arg Gln Ala Ile Glu Phe Val Lys Lys His Lys Leu Lys His
225                 230                 235                 240

Leu Leu Val Glu Thr Ser Val Asp Lys Lys Ala Met Glu Ser Leu Ser
                245                 250                 255

Glu Glu Thr Lys Lys Asp Ile Phe Gly Glu Val Tyr Thr Asp Ser Ile
            260                 265                 270

Gly Lys Glu Gly Thr Lys Gly Asp Ser Tyr Tyr Lys Met Met Lys Ser
        275                 280                 285

Asn Ile Glu Thr Val His Gly Ser Met Lys
    290                 295

<210> SEQ ID NO 12
<211> LENGTH: 334
<212> TYPE: PRT
<213> ORGANISM: Artificial sequence
<220> FEATURE:
<223> OTHER INFORMATION: S. aureus antigen + purification tag

<400> SEQUENCE: 12

Met Ser Tyr Tyr His His His His His His Leu Glu Ser Thr Ser Leu
  1               5                  10                  15

Tyr Lys Lys Ala Gly Leu Ser Ser Lys Ala Met Asp Asn His Pro Gln
             20                  25                  30

Gln Thr Gln Ser Ser Lys Gln Gln Thr Pro Lys Ile Lys Lys Gly Gly
         35                  40                  45

Asn Leu Lys Pro Leu Glu Gln Arg Glu His Ala Asn Val Ile Leu Pro
     50                  55                  60

Asn Asn Asp Arg His Gln Ile Thr Asp Thr Thr Asn Gly His Tyr Ala
 65                  70                  75                  80

Pro Val Thr Tyr Ile Gln Val Glu Ala Pro Thr Gly Thr Phe Ile Ala
                 85                  90                  95

Ser Gly Val Val Val Gly Lys Asp Thr Leu Leu Thr Asn Lys His Val
            100                 105                 110

Val Asp Ala Thr His Gly Asp Pro His Ala Leu Lys Ala Phe Pro Ser
        115                 120                 125
```

-continued

```
Ala Ile Asn Gln Asp Asn Tyr Pro Asn Gly Gly Phe Thr Ala Glu Gln
        130                 135                 140

Ile Thr Lys Tyr Ser Gly Glu Gly Asp Leu Ala Ile Val Lys Phe Ser
145                 150                 155                 160

Pro Asn Glu Gln Asn Lys His Ile Gly Glu Val Val Lys Pro Ala Thr
                165                 170                 175

Met Ser Asn Asn Ala Glu Thr Gln Val Asn Gln Asn Ile Thr Val Thr
                180                 185                 190

Gly Tyr Pro Gly Asp Lys Pro Val Ala Thr Met Trp Glu Ser Lys Gly
        195                 200                 205

Lys Ile Thr Tyr Leu Lys Gly Glu Ala Met Gln Tyr Asp Leu Ser Thr
210                 215                 220

Thr Gly Gly Asn Ser Gly Ser Pro Val Phe Asn Glu Lys Asn Glu Val
225                 230                 235                 240

Ile Gly Ile His Trp Gly Gly Val Pro Asn Glu Phe Asn Gly Ala Val
                245                 250                 255

Phe Ile Asn Glu Asn Val Arg Asn Phe Leu Lys Gln Asn Ile Glu Asp
                260                 265                 270

Ile His Phe Ala Asn Asp Gln Pro Asn Asn Pro Asp Asn Pro Asp
        275                 280                 285

Asn Pro Asn Asn Pro Asp Asn Pro Asn Asn Pro Asp Asn Pro Asn Asn
        290                 295                 300

Pro Asp Glu Pro Asn Asn Pro Asp Asn Pro Asn Asn Pro Asp Asn Pro
305                 310                 315                 320

Asp Asn Gly Asp Asn Asn Asn Ser Asp Asn Pro Asp Ala Ala
                325                 330
```

METHOD FOR DIAGNOSING STAPHYLOCOCCAL INFECTIONS

FIELD OF THE INVENTION

The present invention relates to a method for the serological diagnosis of staphylococcal infections.

BACKGROUND OF THE INVENTION

There are approximately 10 million wearers of prosthetic joints in the world today, and the number of prosthetic joint surgeries continues to increase each year, mainly because of population aging and of the increasing prevalence of obesity, which leads to an excess weight borne by the joints.

Accordingly, it is estimated that by 2020, 2.5 million individuals will undergo surgery to insert a prosthetic joint or to replace an existing prosthetic joint. Besides, an increase in the number of initial joint replacements done in young patients (i.e. under 50 years old) is also observed.

Current figures indicate that approximately 430,000 total hip and knee replacements are done each year in the United States, while approximately 130,000 total hip replacements (THR) and 100,000 total knee replacements (TKR) are implanted or replaced each year in France, where there are currently more than one million wearers of prosthetic joints.

Infection is one of the main complications of joint replacement surgery. In spite of the considerable progress recorded over recent years, prosthetic joint infections are still common, hovering between 0.3% and 2% for total hip replacements, and between 0.5% and 5% for total knee replacements, with the highest rates of infection occurring when existing prosthetic joints are replaced (from 3 days to nearly 20 years following surgery, with an average of 20% of infections occurring within 3 months of joint replacement; 40% occurring between 3 months and 2 years; and 40% occurring after 2 years). These infections are associated with a non-negligible mortality rate (2.5%) as well as with a high morbidity. They usually require one or several additional surgeries and a long course of antibiotics, resulting in significant and often lengthy functional disability. Eventually, the cost of managing these complications is very high, estimated at approximately 60,000 euros per prosthetic joint infection, thereby multiplying by four the cost price of a prosthetic joint when an infection occurs, e.g. reaching a total cost of approximately 80,000 euros for an infected prosthetic hip joint.

50% to 75% of prosthetic joint infections are caused by bacteria from the *Staphylococcus* family, sometimes in a mixed infection along with other species. The two principal species in question are *Staphylococcus aureus* and *Staphylococcus epidermidis*. Staphylococcal prosthetic joint infections are often dormant. The staphylococci assemble and form a biofilm on the surface of the prosthetic implant and survive in a quiescent state characterized by a low metabolic activity. The dormant state of the bacteria as well as the presence of the biofilm considerably reduce inflammatory reactions at the site of the infection and protect the bacteria from antibiotic action.

Prosthetic joint infections are currently managed following essentially two different strategies, namely either surgical debridement (cleaning-debriding) thereby preserving the prosthetic joint, or replacement of the prosthetic joint.

Surgical cleaning and debriding without removing the prosthetic joint (flushing with physiological serum and wound disinfectant), combined with appropriate long-course antibiotics is called for when the infection is detected early following contamination (less than 2 weeks) and when the prosthetic joint has not loosened. This strategy offers the best efficacy vs. risk ratio.

Indeed, where early detection cannot not be achieved, it is necessary to replace the prosthetic joint, either by a one-step or a two-steps replacement method. One-step replacement of the prosthetic joint is a less onerous intervention than the two-steps replacement that requires long hospital stays (6 weeks to 1 year), but it is less effective than the latter. Replacements of prosthetic joints are combined with an antibiotic treatment that is directed against the microorganism(s) that is or are likely to have caused the prosthetic joint infection. Surgical intervention for prosthetic joint infections is associated with mortality rates of 0.4 to 1.2% in 65-year-old patients and 2 to 7% in patients over 80 years old. The risk of the infection recurring remains high after a repeated intervention on a prosthetic joint infection, ranging on average from 10 to 40% according to the location, severity of the lesions and the type of surgical treatment used.

Accordingly, it is of the utmost importance, for the management of prosthetic joint infections, to establish a diagnosis of infection and to determine the causative microorganism as rapidly as possible.

In this regard, clinical symptoms are rarely sufficient to ascertain the infection. In the vast majority of cases, the symptoms simply alert the clinician to a problem and initiate additional examinations required for diagnosis.

Various methods are currently used for establishing the diagnosis of prosthetic joint infection as well as for identifying the causative agent.

Thus, inflammation biomarkers, such as the C-reactive protein (CRP) and the erythrocyte sedimentation rate (ESR) are useful in the diagnosis of prosthetic joint infections. These techniques, however, do not have adequate sensitivity and specificity. Besides, a positive CRP level is not exclusive of a biopsy, since 10-15% of patients undergoing surgery have a normal CRP level. Accordingly, while assaying these biomarkers is prescribed by most surgeons, this mostly appears to be as much due to habit as to the absence of other more sensitive and specific tests taking advantage of serological markers.

Medical imaging techniques are also used. However, radiological diagnosis is not specific enough and only shows signs representative of the later phase of infections, such as loosening of the prosthesis, presence of nodules or cysts, etc. Scintigraphy, most frequently used with gallium, may be useful in diagnosis, but it is often difficult to interpret, thereby leading to a delayed detection of the infection. Magnetic Resonance Imaging and Computer Assisted Tomography scans are usually disregarded because of artifacts due to the presence of the prosthetic joint itself.

Histological analysis of samples obtained during surgery can also be performed. It allows infection to be diagnosed with a sensitivity (i.e. the capacity of detecting infected samples) above 80% and a specificity (i.e. the capacity of detecting non-infected samples) above 90%, but this of course requires a biopsy sample. Besides, depending on the sampling site, significant variations may be observed in the results obtained.

As such, the gold standard in diagnosing prosthetic joint infections remains bacteriological analysis, which involves isolation and culture of the infecting bacteria at the site of infection, from relevant samples. Bacteriological analysis is generally considered as significant if at least 2 out of 5 samples taken during surgery are positive for *S. aureus* and 3 out of 5 samples are positive for other staphylococci. Diagnosis based on samples obtained prior to surgery, e.g. by ultrasound-guided needle aspiration under local anesthesia, or image-guided core-needle biopsy in the operating room under general anesthesia can also be carried out.

Several well-known drawbacks are however associated to bacteriological analysis.

First of all, obtaining pre-operative samples or aspiration liquids for subsequent culture is an invasive procedure which usually requires a surgical procedure carried out under general anesthesia. Secondly, the specificity is often insufficient, since contaminant microorganisms may be isolated, particularly in the case of coagulase-negative staphylococci. Besides, positive results can be hindered due to the initiation of treatment with antibiotics. Thirdly, no standardized techniques have been established for culturing the samples and interpreting the results from the cultures (e.g. the threshold of at least 3 independent positive samples provides excellent specificity (99.6%), but is sometimes achieved to the detriment of sensitivity (65%)). Last but not least, the method may be time consuming since from 48 hours to over 2 weeks might be needed to obtain the results.

In order to overcome the drawbacks associated to bacteriological analysis, in particular as regards the long time needed to obtain the results, it has been suggested to use a serological approach based on the detection of anti-staphylococci antibodies.

Thus, tests to detect anti-α-toxin (or alpha antistaphylolysines), anti-α-ribitol teichoic acid and anti-capsule antibodies have been suggested for systemic infections with *S. aureus* (Bornstein et al. (1992) *Med. Microbiol. Lett.* 1:111-119; Christensson et al. (1993) *J. Infect. Dis.* 163:530-533). However, these tests have been abandoned due to inadequate sensitivity and specificity. In addition, the use of various staphylococcal protein antigens has been suggested for detecting antibodies directed against staphylococcal antigens (WO 2006/005825, U.S. Pat. No. 5,700,928, FR 2 908 890). Nevertheless, these markers, by themselves, do not provide for sufficient sensitivity and specificity. Accordingly, serological methods useful for diagnosing staphylococcal infections have yet to be implemented.

SUMMARY OF THE INVENTION

The present invention arises from the unexpected identification, by the inventors, of particular combinations of *Staphylococcus* protein markers (or antigens) providing for efficient detection of anti-staphylococcal antibodies in biological samples.

Thus, the present invention relates to a serologic method, in particular an in vitro serologic method, for determining if an individual is infected by a *staphylococcus bacterium*, comprising:

determining if antibodies directed against at least 2 proteins comprising a sequence selected from the group consisting of SEQ ID NO: 2, SEQ ID NO: 4, and SEQ ID NO: 6, are present in a biological sample of the individual, and deducing therefrom that the individual is infected by a *staphylococcus bacterium*.

In an embodiment of the invention, the above-defined serologic method comprises determining if antibodies directed against at least one protein comprising SEQ ID NO: 2 and at least one protein comprising SEQ ID NO: 4 and/or SEQ ID NO: 6, are present in a biological sample of the individual.

In another embodiment of the invention, the above-defined serologic method comprises determining if antibodies directed against at least one protein comprising SEQ ID NO: 2 and at least one protein comprising SEQ ID NO: 4, are present in a biological sample of the individual.

In another embodiment of the invention, the above-defined serologic method comprises determining if antibodies directed against at least one protein comprising SEQ ID NO: 2 and at least one protein comprising SEQ ID NO: 6, are present in a biological sample of the individual.

In a further embodiment of the invention, the above-defined serologic method comprises determining if antibodies directed against at least one protein comprising SEQ ID NO: 2, at least one protein comprising SEQ ID NO: 4, and at least one protein comprising SEQ ID NO: 6, are present in a biological sample of the individual.

The present invention also relates to a serologic kit for diagnosing an infection by a *staphylococcus bacterium*, comprising at least two of:

a protein comprising SEQ ID NO: 2, a protein homologous thereto, or a fragment thereof, as defined above;

a protein comprising SEQ ID NO: 4, a protein homologous thereto, or a fragment thereof, as defined above; and a protein comprising SEQ ID NO: 6, a homologous protein thereto, or a fragment thereof, as defined above.

In an embodiment of the invention, the above-defined serologic kit comprises:

a protein comprising SEQ ID NO: 2, a protein homologous thereto, or a fragment thereof, as defined above; and a protein comprising SEQ ID NO: 4, a protein homologous thereto, or a fragment thereof, as defined above; and/or a protein comprising SEQ ID NO: 6, a homologous protein thereto, or a fragment thereof, as defined above.

The present invention also relates to a antigenic method, in particular an in vitro antigenic method, for determining if an individual is infected by a *staphylococcus bacterium*, comprising:

contacting specific capture ligands of at least 2 proteins comprising a sequence selected from the group consisting of SEQ ID NO: 2, SEQ ID NO: 4, and SEQ ID NO: 6, with a biological sample of the individual;

determining if the specific capture ligands are respectively bound to an antigen;

deducing therefrom that the individual is infected by a *staphylococcus bacterium*.

In an embodiment of the invention, the above-defined antigenic method comprises contacting specific capture ligands of SEQ ID NO: 2 and SEQ ID NO: 4 and/or SEQ ID NO: 6.

The present invention also relates to the use, in particular the in vitro use, of specific ligands of at least 2 proteins comprising a sequence selected from the group consisting of SEQ ID NO: 2, SEQ ID NO: 4, and SEQ ID NO: 6, for determining if an individual is infected by a *staphylococcus bacterium*.

In an embodiment of the above-defined use, the invention relates to the use of specific ligands of SEQ ID NO: 2 and SEQ ID NO: 4 and/or SEQ ID NO: 6.

The present invention also relates to an antigenic kit for diagnosing an infection by a *staphylococcus bacterium*, comprising at least two of:

a specific ligand of a protein comprising SEQ ID NO: 2, a specific ligand of a protein comprising SEQ ID NO: 4, and a specific ligand of a protein comprising SEQ ID NO: 6.

In an embodiment of the invention, the above-defined antigenic kit comprises:

a specific ligand of a protein comprising SEQ ID NO: 2, and a specific ligand of a protein comprising SEQ ID NO: 4, and/or a specific ligand of a protein comprising SEQ ID NO: 6.

The present invention also relates to a pharmaceutical composition, in particular for use in the prevention and/or the treatment of an infection by a *staphylococcus bacterium* in an individual, comprising at least two of:
- a protein comprising SEQ ID NO: 2, a protein homologous thereto, or a fragment thereof, as defined above;
- a protein comprising SEQ ID NO: 4, a protein homologous thereto, or a fragment thereof, as defined as defined above; and
- a protein comprising SEQ ID NO: 6, a homologous protein thereto, or a fragment thereof, as defined above;

optionally in association with a pharmaceutically acceptable carrier.

In an embodiment of the invention, the above-defined pharmaceutical composition comprises:
- a protein comprising SEQ ID NO: 2, a protein homologous thereto, or a fragment thereof, as defined above; and
- a protein comprising SEQ ID NO: 4, a protein homologous thereto, or a fragment thereof, as defined above; and/or
- a protein comprising SEQ ID NO: 6, a homologous protein thereto, or a fragment thereof, as defined above.

The present invention also relates to a method for the prevention and/or the treatment of an infection by a *staphylococcus bacterium* in an individual comprising administering the individual with a prophylactically and/or a therapeutically effective amount of at least two of:
- a protein comprising SEQ ID NO: 2, a protein homologous thereto, or a fragment thereof, as defined above;
- a protein comprising SEQ ID NO: 4, a protein homologous thereto, or a fragment thereof, as defined above; and
- a protein comprising SEQ ID NO: 6, a homologous protein thereto, or a fragment thereof, as defined above.

In an embodiment of the invention, the above-defined prevention and/or treatment method comprises comprising administering the individual with a prophylactically and/or a therapeutically effective amount of:
- a protein comprising SEQ ID NO: 2, a protein homologous thereto, or a fragment thereof, as defined above; and
- a protein comprising SEQ ID NO: 4, a protein homologous thereto, or a fragment thereof, as defined above; and/or
- a protein comprising SEQ ID NO: 6, a homologous protein thereto, or a fragment thereof, as defined above.

DETAILED DESCRIPTION OF THE INVENTION

As intended herein, the expressions "*staphylococcus*", "staphylococci", or "staphylococcal" relates to a *bacterium* or to bacteria of the *Staphylococcus* genus. Preferably, the *staphylococcus bacterium* of the invention is a *Staphylococcus aureus*, a *Staphylococcus epidermidis*, a *Staphylococcus capitis*, a *Staphylococcus lugdunensis*, a *Staphylococcus caprae*, a *Staphylococcus warnerii*, or a *Staphylococcus hominis*.

As intended herein the expression "infected" relates to individuals carrying staphylococci as defined above. Preferably, the infected individuals harbour one or several sites wherein multiplication of staphylococci is occurring. Infection by staphylococci often occurs as a consequence of the contact of internal tissues with a foreign material contaminated by staphylococci, in particular in a hospital setting. Accordingly, as intended herein, the infection preferably arises from the implantation of a prosthetic material in the individual, such as a prosthetic joint, notably selected from the group consisting of a knee joint and a hip joint.

As intended herein, the expression "biological sample" includes both the sample as taken and the sample which has been subjected to various treatments, in particular to render it suitable for use in the processes and methods according to the invention. The "biological sample" of the invention can be of any type liable to harbour antibodies, however, it is preferred that the biological sample is selected from the group consisting of a blood sample, a serum sample, a plasma sample, a mucosa-associated lymphoid tissue (MALT) sample, a cerobrospinal fluid sample, an articular liquid sample, a pleural liquid sample, a saliva sample, and an urine sample.

As intended herein, the expression "determining if an individual is infected by a *staphylococcus bacterium*" encompasses establishing a diagnosis or diagnosing an infection by a *staphylococcus bacterium* in an individual. It also encompasses following-up individuals having undergone a surgical operation for implanting, cleaning or replacing a prosthesis. It further encompasses following the evolution of infection by a *staphylococcus bacterium*, in particular within the frame of an anti-staphylococcal treatment. Accordingly, it is preferred that the individual is under treatment by antibiotics.

Determining if antibodies directed against at least 2 proteins comprising a sequence selected from the group consisting of SEQ ID NO: 2, SEQ ID NO: 4, and SEQ ID NO: 6, are present in a biological sample of the individual can be carried out by various methods well known to one of skill in the art. However, determining if antibodies directed against a protein comprising SEQ ID NO: 2, 4, or 6, are present in a biological sample of the individual comprises:
- contacting the biological sample with:
  - a protein comprising SEQ ID NO: 2, 4, or 6; or
  - a homologous protein comprising a sequence sharing at least 80% identity with SEQ ID NO: 2, 4, or 6; or
  - at least one fragment of said protein comprising SEQ ID NO: 2, 4, or 6 or of said homologous protein, wherein said fragment comprises at least 10 amino acids;
- provided said homologous protein and said at least one fragment can be bound by at least one antibody directed against a protein comprising SEQ ID NO: 2, 4, or 6;
- detecting antibodies, preferably IgG, bound to said protein comprising SEQ ID NO: 2, 4, or 6, to said homologous protein or to said at least one fragment.

The proteins comprising SEQ ID NO: 2, 4, and 6, the proteins homologous thereto, and the fragments thereof can present either as polypeptide chains resulting from the in vivo, ex vivo or in vitro polymerisation of amino acids selected from the 20 natural amino acids, or as modified polypeptide chains. As intended herein, in vivo or ex vivo polymerisation notably encompasses production by recombinant means. In vitro polymerisation encompasses production by in vitro translation or by chemical synthesis. Where the polypeptide is modified, it can result from the use of non-natural amino acids during the in vivo, ex vivo or in vitro polymerisation of the polypeptide chain and/or from post-polymerisation modifications. The polypeptide chains can be modified one or several times by identical or different modifications. The modifications can be anywhere in the polypeptide chain, and notably in the peptide backbone, in the amino acid lateral groups, or at the N-terminal or C-terminal extremities of the polypeptide chain. Modifications notably encompass acylation, in particular acetylation, palmytoylation, glypiation, prenylation and myristoylation, ADP-ribosylation, amidation, covalent linkage of a lipid, such as phosphatidylinositol, flavin, an heme, or a nucleotide, covalent or non-covalent cross-linking, cyclisation, disulfide bridge oxidation and reduction, methylation and demethylation, pyroglutamate formation, formylation, gamma-carboxylation, glycosylation, hydroxylation, iodation, oxidation, phosphorylation, selenoylation, sulfatation, racemisation, addition of amino-acids, such as arginylation, or of polypeptides, such as ubiquitinylation.

Besides, where they are obtained by recombinant means, the polypeptide chain of the proteins comprising SEQ ID NO: 2, 4, and 6, the proteins homologous thereto, and the fragments thereof, may also comprise sequences useful for protein purification (so-called purification tags), such as a polyhistidine tags, and optionally a sequence enabling cleavage of these tags, such as protease cleavage sites.

Preferably, the proteins comprising SEQ ID NO: 2, 4, and 6 comprise 350, 400, 500, or 1000 amino acids at the most. More preferably the proteins comprising SEQ ID NO: 2, 4, and 6 respectively consist in SEQ ID NO: 2 or SEQ ID NO: 9, SEQ ID NO: 4 or SEQ ID NO: 10, and SEQ ID NO: 6 or SEQ ID NO: 11.

Preferably, the proteins comprising SEQ ID NO: 2, 4, and 6 are respectively encoded by nucleic acids comprising SEQ ID NO: 1, 3 and 5.

The percentage of identity can be calculated by methods well-known to one of skill in the art. Preferably, the percentage of identity relates to the number identical amino acids obtained for an optimal pairwise alignment (i.e. the alignment maximizing the number of identical amino acids) of the sequence of the homologous protein with SEQ ID NO: 2, 4, or 6, divided by the total number of amino acids in SEQ ID NO: 2, 4 or 6. Alignment can be performed manually or using computer programs such as the EMBOSS-Needle program (Needleman & Wunsch (1970) *J. Mol. Biol.* 48:443-453). Preferably, the percentage of identity is of at least 85%, more preferably of at least 90% percent, and most preferably of at least 95%.

The "fragment" according to the invention relates to any portion of SEQ ID NO: 2, 4 or 6 comprising at least 10 contiguous amino acids. Preferably, the fragment comprises at least 20 amino acids, more preferably at least 30 amino acids, and most preferably at least 40 amino acids. Preferably also, the fragment comprises 100 amino acids at the most, more preferably 80 amino acids at the most, and most preferably 60 amino acids at the most.

As intended herein, the homologous protein as defined above and the at least one fragment as defined above can be bound by at least one antibody directed against a protein comprising SEQ ID NO: 2, 4, or 6. In other words, the homologous protein as defined above and the at least one fragment as defined above comprise at least one of the epitopes of a protein comprising SEQ ID NO: 2, 4, or 6. Accordingly, the homologous protein as defined above and the at least one fragment as defined above should preferably be such that they provide for at least 70%, more preferably at least 80% and most preferably at least 90%, of the sensitivity provided by the protein comprising SEQ ID NO: 2, 4, or 6, measured in the same conditions.

As intended herein, the term "sensitivity" is defined as the percentage of individuals infected by a *staphylococcus*, preferably *S. aureus* or *S. epidermidis*, which biological samples, such as serum samples, are determined to contain antibodies directed against a protein comprising SEQ ID NO: 2, 4, or 6. The determining sensitivity provided by an antigen can be carried out according to various methods well-known to one of skill in the art and notably as illustrated in the following Example 1.

Preferably, in the above-defined serologic method, detecting antibodies can be carried out with specific detecting ligands of the antibodies.

As intended herein, a "ligand" is a compound liable to specifically bind to a target, such as an antibody or an antigen.

The ligand can be of any type but it is preferred that it is an antibody, an aptamer, or a peptide obtained by phage display.

An "antibody" as intended herein relates to antibodies belonging to any species, such as human, mouse, rat, rabbit, goat, or camelidae species. The antibody can also be a chimeric antibody, i.e. an antibody which comprises parts originating from different species. Preferred chimeric antibodies are so-called "humanized" antibodies, wherein the constant parts (CH and CL) are of human origin and the variable parts (VH and VL) are of another species, such as mouse for instance. The antibody of the invention can be produced by any method known the man skilled in the art, such as by animal immunization, or by recombinant or synthetic methods for instance. Besides, an "antibody" according to the invention also encompasses antibody fragments which comprise at least one of the paratopes of said antibody, such as Fab, F(ab')2, scFv fragments as well as camelidae single-chain antibodies. The antibody of the invention can be a polyclonal antibody, in particular a monospecific polyclonal antibody, or a monoclonal antibody.

"Aptamers" are well-known by the one skilled in the art. Aptamers are compounds of a nucleotide, in particular a ribonucleotide or desoxyribonucleotide, or a peptide nature able to bind specifically to a target, in particular a protein target. The aptamers of a nucleotide nature and the production thereof are described, in particular, by Ellington et al. (1990) Nature 346:818-22 and Bock et al. (1992) Nature 355:564-6. The aptamers of a peptide nature and the production thereof are described, in particular, by Hoppe-Seyler et al. (2000) J. Mol Med. 78:426-30.

"Phage display" denotes a technique for selecting polypeptide ligands expressed on the capsid of a bacteriophage and encoded by a nucleic sequence inserted into the capsid encoding gene. This method is well known by the one skilled in the art and is described, in particular, by Scott & Smith (1990) Science 249:386-390, and Marks et al. (1991) J. Mol. Biol. 222:581-597. Preferably, the polypeptide obtainable by phage display is an scFv-type polypeptide (single-chain variable fragment). This technique is described, in particular, by Winter et al. (1994) Annu. Rev. Immunol. 12:433-455.

The term "specific", when it refers to recognition of a ligand or binding of a ligand to a first target, such as an antigen or an antibody, means that the ligand interacts with the first target without interacting substantially with another target which does not structurally resemble the first target.

In the above-defined antigenic method, determining if the capture ligands are respectively bound to an antigen can be carried out by using a detection ligand which is specific of said antigen but preferably binds to said antigen by recognition of an another binding site (i.e. epitope) than the recognition site of said capture ligand.

Preferably, the "detection ligand" according to the invention is labelled. The term "labelled" refers both to a direct labelling and to an indirect labelling (for example, by means of other ligands, themselves directly labelled, or using reagents of a labelled "affinity pair", such as, but not exclusively, the labelled avidin-biotin pair, etc.). Preferably, the label is a radioisotope, an enzyme or a fluorophore.

As will be clear to one of skill in the art, in the above-defined serologic method, the protein comprising SEQ ID NO: 2, 4, or 6, the homologous protein or the fragment can be used as a capture antigen.

Methods using capture antigens or ligands and detection ligands are well known to one of skill in the art and can be carried out in accordance with various well-known formats, for example in solid or homogeneous phase, in one or two steps, by a sandwich method or by a competitive method.

Preferably, the capture antigen or ligand is immobilised on a solid phase. By way of non-limiting examples of solid phase, microplates could be used, in particular polystyrene microplates, solid optionally paramagnetic particles or beads, or even polystyrene or polypropylene test tubes, glass, plastic or silicon chips, etc.

Summary of the sequence described herein:

| Sequence description | SEQ ID NO: |
|---|---|
| 2B6 nucleotide sequence | 1 |
| 2B6 protein sequence | 2 |
| 7B3 nucleotide sequence | 3 |
| 7B3 protein sequence | 4 |
| 5G1 nucleotide sequence | 5 |
| 5G1 protein sequence | 6 |
| 7A7 nucleotide sequence | 7 |
| 7A7 protein sequence | 8 |
| 2B6 + His tag protein sequence | 9 |
| 7B3 + His tag protein sequence | 10 |
| 5G1 + His tag protein sequence | 11 |
| 7A7 + His tag protein sequence | 12 |

EXAMPLES

Example 1

Serum samples obtained from patients were assayed using combinations of staphylococcal antigens according to the invention.

1. Materials and Methods 11 or 15 sera from patients with a *Staphylococcus epidermidis*-infected prosthesis with and 12 or 13 sera from patient with a *Staphylococcus aureus*-infected prosthesis were used and compared to 47 control sera from healthy individuals. Determination of the infected status of the individuals was carried out by bacteriological analysis.

Antigens 2B6 (SEQ ID NO: 9), 7B3 (SEQ ID NO: 10), 5G1 (SEQ ID NO: 11), and 7A7 (SEQ ID NO: 12) were recombinantly produced in *Escherichia coli* and purified according to usual methods, such as described in Lavallie (1995) "Production of recombinant proteins in *Escherichia coli*" Unit 5.1. *Current Protocols in Protein Science*; Scopes (1995) "Strategies for protein purification" Unit 1.2. *Current Protocols in Protein Science*.

The antigens were covalently attached to surface carboxyl groups of MicroPlex Microspheres (Luminex®) using N-hydroxysulfosuccinimide (sulfo-NHS) and 1-ethyl-3-(3-dimethylaminopropyl)carbodiimide hydrochloride (EDC) according the manufacturer's instructions. 25 μg were used for attachment to 5,000,000 microspheres.

Detection of serum antibodies was carried out according to the manufacturer's instructions. Briefly, antigen-coupled microspheres were added to the wells of a multiwell plate and contacted with the various sera for a time sufficient to allow antibody-antigen complexes to be formed. After discarding the unreacted serum and washing theplate, a phycoerythrin-labeled anti-IgG antibody was added to the microspheres. Antibody-antigen complexes were further revealed by determining the mean fluorescence intensity (MFI) for each serum with a Luminex® analyzer.

The cut-off values for each serologic assay were determined by Receiver Operating Characteristics (ROC) curve analysis as described in the guideline GP10-A of December 1995 from the National Committee for Clinical Laboratory Standards (NCCLS) as the values yielding a maximum efficiency. The efficiency is defined as the ratio of the sum of the true positive samples and the true negative samples obtained with the serologic assays by the total number of samples assayed. True positive and negative samples are samples which are respectively determined as being positive and negative both using the serologic assay of the invention and bacteriological analysis. A sample was then considered positive if the antibody titer exceeded the defined cut-off value.

The antigen combination was analyzed by discriminant function analysis before setting a cut-off value by ROC curve analysis as indicated above.

2. Results

TABLE 1 diagnosis potency of the 7B3-2B6 combination

| | Tested antigens | | | | |
|---|---|---|---|---|---|
| Ratio of positive sera | 7B3 | 2B6 | 7A7 | 7B3 + 2B6 | 7B3 + 7A7 |
| *S. epidermidis* positive patients (11) | 64% | 55% | 36% | 73% | 55% |
| *S. aureus* positive patients (12) | 67% | 42% | 42% | 83% | 58% |
| *S. epidermidis* + *S. aureus* (23) | 65% | 48% | 39% | 78% | 57% |
| Healthy individuals (47) | 9% | 9% | 9% | 9% | 9% |

The 2B6 and 7A7 antigens individually enabled detecting the same ratio of patients infected with *S. aureus* (i.e. 42%). However, only the 2B6-7B3 combination is shown to be of interest since it allows a 16% increase in sensitivity (67% of the *S. aureus* positive patients are detected with 7B3 alone vs. 83% of the same patients are detected with the 7B3-2B6 combination). In contrast, the 7A7-7B3 combination does not appear to be of any interest since it provides for less sensitivity than 7B3 alone.

In conclusion, it appears impossible to predict the sensitivity, in particular an increase in sensitivity, of a combination of antigens in view of their individual sensitivities. Besides, the 2B6-7B3 combination presents unexpected diagnosis potency for the detection of infections by staphylococci.

TABLE 2 diagnosis potency of the 5G1-2B6 combination

| | Tested antigens | | | | |
|---|---|---|---|---|---|
| Ratio of positive sera | 5G1 | 2B6 | 7A7 | 5G1 + 2B6 | 5G1 + 7A7 |
| *S. epidermidis* positive patients (15) | 47% | 47% | 40% | 53% | 53% |
| *S. aureus* positive patients (13) | 69% | 31% | 38% | 77% | 69% |
| *S. epidermidis* + *S. aureus* (28) | 57% | 39% | 39% | 64% | 61% |
| Healthy individuals (47) | 6% | 6% | 6% | 6% | 6% |

In this assay, the 2B6 antigen appears to be less potent than the 7A7 antigen for detecting patients infected with *S. aureus* (31% for 2B6 vs. 38% for 7A7). The 2B6-5G1 combination, however, offers a better sensitivity than the 7A7-5G1 combination. Thus, 77% of the *S. aureus*-infected patients are detected by the 2B6-5G1 combination, thereby providing for an 8% increase in sensitivity with respect to 5G1 alone. In contrast, the 5G1-7A7 combination provides for no increase in sensitivity.

In conclusion, the 2B6-5G1 appears to be unexpectedly well suited for the detection of infections by staphylococci.

Example 2

The serological status of patients infected by a *staphylococcus* and undergoing antibiotherapy was monitored with the 5G1-2B6 combination of the invention.

1. Materials and Methods

A total of 16 sera originating from 8 patients carrying a prosthesis infected with *S. epidermidis* or *S. aureus* were used. Two sera were analyzed for each patient. The first serum (serum 1) was obtained from the patient during the course of a surgical operation aiming at cleaning an infected prosthesis. The second serum was obtained after 3 months of treatment by antibiotics.

Detection of serum antibodies was performed as indicated in Example 1.

The variation in the antigenic response of the infected patients was then determined by calculating the ratio $(MFI_{serum\ 2} - MFI_{serum1})/MFI_{serum\ 1}$ where MFI represents de Mean Fluorescence Intensity obtained for each serum. A negative variation is indicative of an efficient antibiotherapy.

2. Results

Table 3 shows the variation of the antigenic response of patients infected by *S. epidermidis* or *S. aureus* after 3 months of treatment by antibiotics

| | Tested antigen | | |
|---|---|---|---|
| Patient | 5G1 | 2B6 | 5G1 + 2B6 |
| 1 | −23% | −17% | −41% |
| 2 | −22% | −34% | −66% |
| 3 | −27% | −30% | −39% |
| 4 | −48% | −32% | −57% |
| 5 | −67% | −26% | −76% |
| 6 | −78% | −48% | −120% |
| 7 | −78% | −32% | −128% |
| 8 | −85% | −28% | −195% |

It can be seen that for each patient the use of the combination is advantageous since the percentage of variation is more important than for each antigen alone, thereby offering an increased sensitivity. For certain patients, the percentage of variation obtained for the combination is unexpectedly more important than would be expected by adding the percentage of variation of each antigen, which is indicative of a synergic effect.

The invention claimed is:

1. A method for determining if an individual is infected by a *Staphylococcus bacterium*, comprising:
   determining if antibodies directed against at least one protein comprising sequence SEQ ID NO: 2 and at least one protein comprising sequence SEQ ID NO: 4, are present in a biological sample of the individual, and
   deducing therefrom that the individual is infected by a *Staphylococcus bacterium*,
   wherein determining if antibodies directed against at least one protein comprising sequence SEQ ID NO: 2 and at least one protein comprising sequence SEQ ID NO: 4, are present in a biological sample of the individual comprises the steps of:
   (a) contacting the biological sample with at least:
      a purified protein comprising SEQ ID NO: 2; and
      a purified protein comprising SEQ ID NO: 4; and
   (b) detecting antibodies bound to said protein comprising SEQ ID NO: 2 and to said protein comprising SEQ ID NO: 4.

2. The method of claim 1, wherein said method further comprises determining if antibodies directed against at least one purified protein comprising SEQ ID NO: 6, are present in a biological sample of the individual.

3. The method of claim 1, wherein the *Staphylococcus bacterium* is *Staphylococcus aureus, Staphylococcus epidermidis, Staphylococcus capitis, Staphylococcus lugdunensis, Staphylococcus caprae, Staphylococcus warnerii*, or *Staphylococcus hominis*.

4. The method of claim 1, wherein the antibodies are IgG.

5. The method of claim 1, wherein the individual has been implanted a prosthetic joint.

6. The method of claim 1, wherein the individual has been implanted a prosthetic joint selected from the group consisting of a knee joint and a hip joint.

7. The method of claim 1, wherein the biological sample is selected from the group consisting of a blood sample, a serum sample, a plasma sample, a mucosa-associated lymphoid tissue (MALT) sample, a cerobrospinal fluid sample, an articular liquid sample, a pleural liquid sample, a saliva sample, and an urine sample.

8. The method of claim 1, wherein the individual is under treatment by antibiotics.

9. A pharmaceutical composition comprising:
   a purified protein comprising SEQ ID NO: 2 and
   a purified protein comprising SEQ ID NO: 4, and
   optionally in association with a pharmaceutically acceptable carrier.

10. A kit for diagnosing an infection by a *staphylococcus bacterium*, comprising at least a purified protein comprising SEQ ID NO: 2 and a purified protein comprising SEQ ID NO: 4.

11. The kit according to claim 10, wherein said kit further comprises a purified protein comprising SEQ ID NO: 6.

12. A method for treating an infection by a *Staphylococcus bacterium* in an individual, said method comprising administering to the individual the pharmaceutical composition of claim 9.

13. A method for inducing an immune response against an infection by a *Staphylococcus bacterium* in an individual, said method comprising administering to the individual the pharmaceutical composition of claim 9.

14. The method of claim 12, further comprising administering a purified protein comprising SEQ ID NO: 6.

15. The method of claim 13, further comprising administering a purified protein comprising SEQ ID NO: 6.

* * * * *